United States Patent
Kikuchi et al.

(10) Patent No.: US 7,811,829 B2
(45) Date of Patent: Oct. 12, 2010

(54) MEASURING PROBE AND PRODUCTION PROCESS THEREOF

(75) Inventors: Yoshihiko Kikuchi, Kawasaki (JP); Hiroshi Suzuki, Sagamihara (JP); Takeshi Imamura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 12 days.

(21) Appl. No.: 11/808,139

(22) Filed: Jun. 7, 2007

(65) Prior Publication Data

US 2008/0000308 A1  Jan. 3, 2008

(30) Foreign Application Priority Data

Jun. 8, 2006  (JP) ............................. 2006-160077

(51) Int. Cl.
*G01N 33/543* (2006.01)

(52) U.S. Cl. .................... 436/518; 435/7.1; 435/283.1; 435/287.1; 435/287.2; 436/528; 436/530; 436/532

(58) Field of Classification Search .............. 435/7.1, 435/283.1, 287.1, 287.2; 436/518, 528, 530, 436/532
See application file for complete search history.

(56) References Cited

U.S. PATENT DOCUMENTS

| | | | | |
|---|---|---|---|---|
| 4,974,929 A | * | 12/1990 | Curry | 385/12 |
| 5,242,793 A | | 9/1993 | Kariyone et al. | 435/4 |
| 5,258,043 A | * | 11/1993 | Stone | 264/108 |
| 5,395,754 A | * | 3/1995 | Lambotte et al. | 435/7.4 |
| 5,665,597 A | | 9/1997 | Imamura et al. | 435/253.3 |
| 5,679,568 A | | 10/1997 | Imamura et al. | 435/262.5 |
| 5,693,527 A | | 12/1997 | Imamura | 435/262 |
| 5,726,064 A | * | 3/1998 | Robinson et al. | 436/514 |
| 5,803,664 A | | 9/1998 | Kawabata et al. | 405/128 |
| 5,807,736 A | | 9/1998 | Kozaki et al. | 435/262.5 |
| 5,854,059 A | | 12/1998 | Kozaki et al. | 435/262 |
| 5,863,789 A | | 1/1999 | Komatsu et al. | 435/262 |
| 5,945,331 A | | 8/1999 | Kozaki et al. | 435/262 |
| 5,962,305 A | | 10/1999 | Mihara et al. | 435/262.5 |
| 5,993,658 A | | 11/1999 | Kato et al. | 210/611 |
| 6,004,772 A | | 12/1999 | Imamura et al. | 435/34 |
| 6,004,943 A | * | 12/1999 | Shi et al. | 514/44 R |
| 6,017,746 A | | 1/2000 | Imamura et al. | 435/252.1 |

(Continued)

FOREIGN PATENT DOCUMENTS

JP  61-86644  5/1986

(Continued)

OTHER PUBLICATIONS

Kagaku Binran, (Handbook of Chemistry), 5th ed., Applied Chemistry I, Chap. 10, Sec. 5, Kagaku Dojin, Tokyo, pp. II-665-II-679. (with partial Translation).

*Primary Examiner*—Melanie Yu
(74) *Attorney, Agent, or Firm*—Fitzpatrick, Cella, Harper & Scinto

(57) ABSTRACT

To provide a measuring probe excellent in sensitivity and reproducibility, simple operation in the protein immobilization onto a support can prevent peeling or damage. A layer containing a protein is adsorbed onto a support surface to fully encircle the long axis of the support, and the adsorbed layer is treated for cross-linking with a cross-linking agent in a concentration of 1 to 5 moles to 1 mole of the protein.

15 Claims, 2 Drawing Sheets

U.S. PATENT DOCUMENTS

| | | | | |
|---|---|---|---|---|
| 6,096,530 A | 8/2000 | Kato et al. | ............... | 435/253.3 |
| 6,103,535 A * | 8/2000 | Pilevar et al. | ............... | 436/518 |
| 6,316,606 B1 | 11/2001 | Kishi et al. | ................. | 536/4.1 |
| 6,319,706 B1 | 11/2001 | Kawaguchi et al. | ...... | 435/293.1 |
| 6,472,191 B1 | 10/2002 | Yano et al. | ................. | 435/189 |
| 6,479,621 B2 | 11/2002 | Honma et al. | ................. | 528/361 |
| 6,586,562 B2 | 7/2003 | Honma et al. | ................. | 528/361 |
| 6,649,381 B1 | 11/2003 | Honma et al. | ................. | 435/135 |
| 6,660,516 B1 | 12/2003 | Imamura et al. | ......... | 435/252.8 |
| 6,686,439 B2 | 2/2004 | Kenmoku et al. | ........... | 528/272 |
| 6,803,444 B2 | 10/2004 | Suzuki et al. | ............... | 528/361 |
| 6,808,854 B2 | 10/2004 | Imamura et al. | ............ | 430/110 |
| 6,828,074 B2 | 12/2004 | Yano et al. | ................. | 430/109.1 |
| 6,830,613 B2 | 12/2004 | Mihara et al. | ............ | 106/217.9 |
| 6,855,472 B2 | 2/2005 | Imamura et al. | ......... | 430/109.4 |
| 6,858,367 B2 | 2/2005 | Yano et al. | ................. | 430/109 |
| 6,858,417 B2 | 2/2005 | Yano et al. | ................. | 435/189 |
| 6,861,496 B2 | 3/2005 | Kenmoku et al. | ........... | 528/272 |
| 6,861,550 B2 | 3/2005 | Honma et al. | ................. | 560/53 |
| 6,864,074 B2 | 3/2005 | Yano et al. | ................. | 435/189 |
| 6,867,023 B2 | 3/2005 | Honma et al. | ............... | 435/135 |
| 6,869,782 B2 | 3/2005 | Kenmoku et al. | ........... | 435/130 |
| 6,900,295 B2 | 5/2005 | Kishi et al. | ................... | 536/4.1 |
| 6,908,720 B2 | 6/2005 | Kenmoku et al. | ............. | 430/97 |
| 7,105,340 B2 * | 9/2006 | Jan et al. | ................. | 435/287.9 |
| 7,169,598 B2 | 1/2007 | Honma et al. | ............ | 435/253.3 |
| 7,276,368 B2 * | 10/2007 | Saaski | ..................... | 435/287.1 |
| 7,416,705 B2 * | 8/2008 | Lee et al. | .................... | 422/100 |
| 2003/0077761 A1 * | 4/2003 | Parrow et al. | .............. | 435/91.2 |
| 2003/0108917 A1 * | 6/2003 | Huh et al. | ....................... | 435/6 |
| 2004/0121356 A1 * | 6/2004 | Yamagata et al. | ............. | 435/6 |
| 2004/0166508 A1 * | 8/2004 | Pawlak et al. | ................. | 435/6 |
| 2005/0158755 A1 * | 7/2005 | Lee et al. | ....................... | 435/6 |
| 2006/0000772 A1 * | 1/2006 | Sano et al. | .................. | 210/635 |
| 2006/0099111 A1 | 5/2006 | Kikuchi et al. | ............. | 422/68.1 |
| 2006/0183235 A1 | 8/2006 | Hashimoto et al. | ............ | 436/86 |
| 2007/0054315 A1 | 3/2007 | Imamura et al. | ............. | 435/7.1 |
| 2007/0178522 A1 | 8/2007 | Shiotsuka et al. | ............ | 435/7.1 |

FOREIGN PATENT DOCUMENTS

| | | | |
|---|---|---|---|
| JP | 1-235579 | | 9/1989 |
| JP | 2-236153 | | 9/1990 |
| WO | 2004/051231 | * | 6/2004 |

\* cited by examiner

MEASURING PROBE AND PRODUCTION PROCESS THEREOF

BACKGROUND OF THE INVENTION

1. Field of the Invention

The present invention relates to a measuring probe prepared by immobilizing a protein on a support surface probe to detect a pathogen, a biologically active agent, a chemical substance etc.

2. Description of the Related Art

Probes prepared by immobilizing a protein that specifically interacts to a certain substance are used as measuring probes to detect various substances such as biomaterials. For such measuring probes, a protein that selectively reacts with a specific analyte substance such as enzymes and antibodies is immobilized on a surface of a support made of, e.g., glass, metals, paper or resins.

To immobilize a protein to a support, one of the sure methods is to covalently bonding a specific substituent on the support and a specific substituent of the protein, which can provide a relatively robust and stable immobilized layer.

However, previous introduction of such a substituent may be difficult due to the material of the support, or may be undesirable in view of complication of preparation steps.

Immobilization of a protein on a support other than the above covalent bonding to the support includes adsorption to the support by electrostatic force (ion binding method), adsorption by using association based on hydrophilicity/hydrophobicity (physical adsorption method) (refer to, for example, Kagaku Binran (Chemistry handbook) 5th edition, Applied Chemistry I, Chapter 13, Section 5 (Tokyo Kagaku Dojin)). The latter method is especially useful because it enables easy and effective protein adsorption to a resin material generally used as a structure material such as polystyrene.

Even when covalent bonding between the protein and the support is not carried out, cross-linking reaction between the molecules to be immobilized (protein molecules) may be carried out to aid the immobilization (hereinafter referred to as a cross-linking method). By the cross-linking method, the molecules to be immobilized are not bonded to the support but they integrally form one fixed layer, which will reduce mobility and increase adhesiveness to the support surface. Japanese Application Laid-Open No. S61-086644 discloses a production method of a sensor using an enzyme electrode where the enzyme is cross-linked to other proteins. It also discloses a two-step method where the application of a protein solution is followed by impregnation of a solution containing a cross-linking agent. Although the cross-linking method is simple in operation, there is a risk that the excess cross-linking agent may cause undesirable change in physical properties and functions. Japanese Application Laid-Open No. H02-236153 discloses optimization of the component ratio by weight of the cross-linking agent in production of a selective permeation membrane made by cross-linking a protein and a non-proteinaceous polymer.

As a similar technique, a protein is immobilized on a support with a synthetic polymer. Japanese Application Laid-Open No. H01-235579 discloses immobilization of an enzyme onto the surface of a fibrous support using a photocurable resin. Such a system is often applied to bioreactors.

SUMMARY OF THE INVENTION

Immobilization by the cross-linking method is simple in operation and applicable to a wide range of analytes, but it has a disadvantage that the physical immobilization strength of the protein layer is not sufficient to be applied to a measuring probe. The protein layer may peel off from the support when the solution contacting the probe moves vigorously, or when the solution is sent continuously for a long time, which may lead to insufficient measuring sensitivity or poor reproducibility of the measurement data. Also a caution should be taken so that the portion of the protein participating detection is not damaged by the excess cross-linking reaction in consideration of the use as a measuring probe.

An object of the present invention is to provide a measuring probe excellent in sensitivity and reproducibility by reducing the damage of the protein layer and peeling off of the layer.

Another object of the present invention a method of producing a measuring probe excellent in sensitivity and reproducibility, characterized by that the protein is immobilized with little protein damage and with the simplicity of the cross-linking method.

One aspect of the present invention is a measuring probe for detecting a specific object in a sample in contact with the sample, where the probe comprises a protein layer in a form of a complete circle (a circular form), and the protein layer has been cross-linked by using a solution containing a cross-linking agent in a concentration 1-5 times as much as that of the protein.

The protein layer is preferably formed to have a portion fully encircling one of the axes of the support.

Further, another aspect of the present invention is a method of producing a measuring probe for detecting a specific analyte in a sample in contact with the sample, where the method comprises a step of forming on the support surface a protein layer in a circular form, where the protein layer is cross-linked by using a solution containing a cross-linking agent in a concentration 1-5 times as much as that of the protein.

The third aspect of the present invention is a measuring probe to detect the presence or absence of a target substance in a sample or the concentration thereof, the probe comprises a support having a columner optical waveguide thereon, a layer containing a protein formed on the surface of the optical waveguide to enclose it, where the protein molecules constituting the protein-containing layer are cross-linked with a cross-linking agent.

According to the present invention, peeling of the protein layer coating the support is suppressed, which will prevent lowering of the reproducibility and responsiveness of the measuring probe caused by physical stimulation.

The measuring probe of the present invention has a protein layer formed on the surface of an optical waveguide to enclose it, where the protein molecules in the protein layer are cross-linked with a cross-linking agent, hence peeling of the protein layer is suppressed. Also it has advantages that cross-linking treatment between the protein layer and the waveguide surface is not required and stable and high detection sensitivity is achieved.

Further features of the present invention will become apparent from the following description of exemplary embodiments with reference to the attached drawings.

BRIEF DESCRIPTION OF THE DRAWINGS

FIG. 1A: a fiber-like configuration, FIG. 1B: brush-like configuration, FIG. 1C: mesh-like configuration, FIG. 1D: non-linear configuration, and FIG. 1E: open ring-like configuration (C letter form).

DESCRIPTION OF THE EMBODIMENTS

Figure 1A:
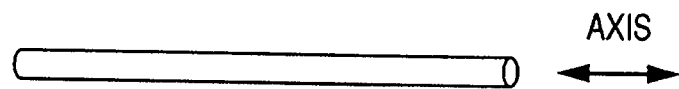
FIGS. 1A, 1B, 1C, 1D and 1E are schematic diagrams to show examples of appropriate configurations of the measuring probe of the present invention.

In the present invention, the so-called measuring probe comprises a support and a protein layer in a circular shape formed on the support surface. The support of the probe is an insoluble support having a structure suitable for a chip to be used in order to detect a specific analyte in a sample in contact with the sample. The support has at least one axis, and a preferred shape of the axis is an almost columnar, fiber-like shape.

A preferable support has an optical waveguide or has a function of optical waveguide by itself.

In the present invention, the probe is characterized in that at least part of the support surface is coated with a protein layer, and the detection is carried out by the protein itself or by another detection component held by the protein, e.g., provided on the surface of the protein layer.

Coating is carried out by the cross-linking method for simplifying the manufacture, and the support may be made of a material having a difficulty in forming a covalent bond with a substance to be held on the support, for example, a protein. Exemplifying materials are hydrophobic resins such as polystyrene and polyethylene, those frequently used for vessels.

In the present invention, immobilization based on the cross-linking method can prevent peeling of the protein layer from the support, where the protein layer is formed in a circular form on the support surface. The circular structure of the protein layer prevents the layer from peeling off from the support.

A representative structure is such that the support (solid carrier) has an axis extending in a certain direction. In this case, an example probe is formed to have at least a part fully encircling one axis of the support. That is, the support has a configuration having one or more axes, and a protein layer is provided on the support to encircle a cross section (e.g., at right angles) of any or a given axis or axes. More specifically, a columnar support always has a line fully encircling it. When a two-dimensional protein layer is formed and immobilized by cross-linking the protein molecules or by cross-linking a protein and other components, owing to the existence of cross-linked complex corresponding to the above line, the protein layer has a holding function to the support. This may prevent peeling and loss of the protein layer, even when any covalent bonds are not formed between the protein layer and the support.

In general, an immobilization method of a protein to a support in order to reduce or prevent peeling of the protein from the support is to bond a specific substituent on the support and a specific substituent on the protein by a covalent bonding, which can provide a relatively strong and stable immobilized layer.

According to the study by the inventors, such a method has problems that previous introduction of such substituents may be difficult or the process may be complicated and cumbersome.

In the present invention, immobilization is assisted by cross-linking between the molecules to be immobilized such as protein molecules (the cross-linking method).

According to the cross-linking method, the molecules to be immobilized and the support are not bonded but the molecules form an integral layer, which will reduce the mobility and increase the adhesiveness to the support surface.

In the production method of a measuring probe having an optical waveguide of the present invention, protein molecules such as antibody or antigen protein are cross-linked.

The cross-linking method includes a two-step process where first a protein solution is applied and then a solution containing a cross-linking agent is applied.

The cross-linking method used in the present invention is simple in operation and capable of forming a measuring probe having preferred properties and functions by optimizing the weight ratio of the cross-linking agent.

The protein layer may contain non-protenaceous polymers to cross-link such polymer molecules.

Figure 1B:
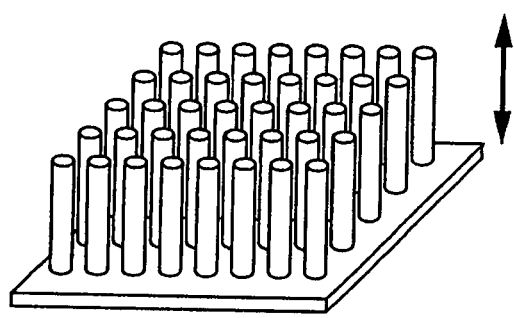
Figure 1C:
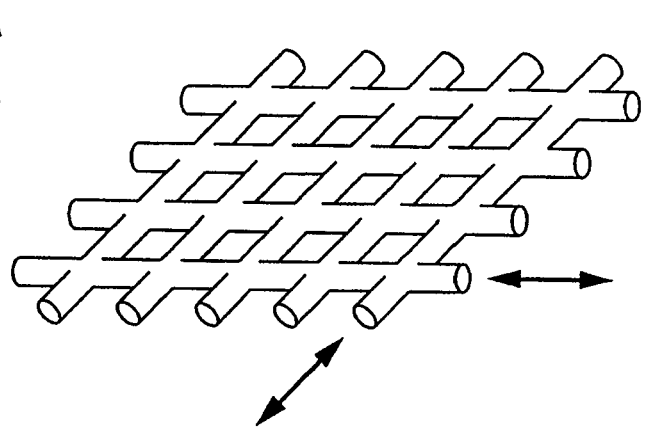
Figure 1D:
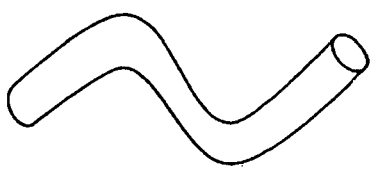
Figure 1E:
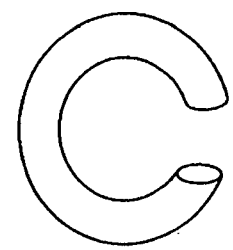

The preferred configuration of the support is a columnar configuration, although even a slab configuration is applicable by using the both surfaces and sides thereof. With a columnar configuration, more uniform and continuous cross-linked complex can be obtained. Specific examples are fiber-like, brush-like, mesh-like configurations (FIGS. 1A to 1C). The configuration may be one obtained by bending or twisting one of the above configurations, such as dendric, ring, and pile configurations. The configuration may be a non-linear form or an open ring-form (C letter configuration) as shown in FIGS. 1D and 1E.

In an embodiment of the present invention, the protein is an antibody or antigen, the support has a fiber type optical waveguide for optical detection. Specifically, the present invention provides a measuring probe useful for fluorescence immunoassay by evanescent wave excitation using a columnar probe.

The measuring probe of the present invention mainly uses an antibody as the detection protein, and the support has a columnar shape. Ordinarily, when an antibody is immobilized reducing its peeling, the antibody is immobilized by a covalent bond. Such a method, however, has a drawback that the support surface may become rough, and it is difficult to control the roughness.

On the other hand, according to the present invention, a cross-linking method using a cross-linking agent is applied, which method has been used as a method to immobilize an enzyme onto an electrode, so that it is possible to control the uniformity of the solid surface.

The uniformity of the solid surface is very important for the fluorescence immunoassay by evanescent wave excitation, since the roughness of the solid surface seriously affect the signal variation.

By using the measuring probe of the present invention, the uniformity of the solid surface can be secured and stable signals can be obtained.

In order to enhance the performance of the measuring probe of the present invention in the fluorescence immunoassay using evanescent wave excitation, it is desirable to further increase the strength of the protein layer by cross-linking while maintaining function of the immobilized protein.

In order to improve the strength of the protein layer by cross-linking while maintaining the protein function, the molar ratio of the cross-linking agent to the protein is desirably about 1:1 after the reaction. Thus it is desirable that the feed ratio is feasible for it. In other words, it was found suitable to use a solution of cross-linking agent of a molar concentration (mol/L) 1-5 times as high as that of the protein present on the support before the cross-linking reaction. The concentration range of 1-5 times was set in consideration of reduction in the reaction product due to the deactivation of the cross-linking agent in the solution or steric hindrance of the protein, to be determined according to the materials and reaction conditions to be used. Here, the protein concentration on the support surface means the mol number of the protein contained in the layer formed on the support surface divided by the volume of the layer. The volume is calculated from the coated surface area of the support and the substantial layer thickness, including voids and the volume occupied by the components other than the protein.

The cross-linking agent may affect the protein function even within the above concentration range, but the influence on detection function is negligible in practical use.

The molar concentration of the cross-linking agent lower than that of the protein is not preferred since it results in insufficient cross-linking, making insufficient the strengthening effect by the cross-linked protein chain encircling the columnar part of the support.

On the other hand, the concentration of the cross-linking agent higher than that of the protein 5-fold or more is not preferable, since the possibility of damage on protein function will increase.

The proteins having detection function (hereinafter referred to as detection protein) may be antibodies, antigens, enzymes, receptors etc. Two or more proteins selected from the above groups may be used in combination. Further, according to necessity, two or more species of antibodies and antigens, in some cases, enzymes and receptors, may be used in combination. Compared with enzymes, antibodies have exposed recognition portions, so that they have higher possibility to be damaged by cross-linking reaction. Thus the above component ratio is more suitably applied to antibodies.

Alternatively, the above-described cross-linked protein layer may be formed on the given surface of the support as a subbing layer, on which the above-described detection protein may be bonded as a component to detect a specific analyte. This method is useful when less damage of the detection protein by the cross-linking reaction is desired or when the orientation of the detection protein is very important. Underlayer proteins suitable for such purposes include avidine, and protein G. Selective connection to avidine can be carried out via biotin. Protein G is useful to connect the Fc portion of an antibody to the support. In this mode, it is possible to use detection components such as nucleic acid bases, saccharide chain, metal coordinates, other than proteins.

In addition, the underlying protein may prevent non-specific adsorption, so that it may be more useful than synthetic polymers according to the analyte to be measured. Such underlying proteins include albumins and caseins.

The components of the protein layer may include two or more proteins or non-proteinaceous components. For example, the layer may also contain other cross-linkable polymers in order to provide a space around the detection protein which is convenient for detection reaction, or to adjust the strength of the protein layer. Such polymers may be cellulose and polyvinyl alcohol.

The antibody used in the measuring probe of the present invention as a detecting protein may be any molecule as long as it contains a region having a so-called immunoglobulin fold structure. Usually, an antibody such as IgG, IgM, IgA, IgE and IgD or a complex thereof is used, but an antibody fragment such as Fab'2, Fab, Fv, even VH and VL can be used by itself. Further, it is possible to use an antibody fragment complex such as scFv, Diabody, Triabody and Tetrabody, which are genetically engineered single stranded polypeptides composed of antibody fragments linked using a peptide linker.

The target substances that can be detected by the immunoassay using the measuring probe of this invention are classified into non-biological substances and biological substances.

Non biological substance of which detection has a great potential in industry are pollutants such as PCBs differing in chlorine substitution number and position, dioxins differing in chlorine substitution number and position, so-called environmental hormones (endocrine-disturbing substances), e.g., hexachlorobenzene, pentachlorophenol, 2,4,5-trichloroacetic acid, 2,4-dichlorophenoxyacetic acid, amitrole, atrazine, alachlor, hexachlorocyclohexane, ethylparathion, chlordane, oxychlordene, nonachlor, 1,2-dibromo-3-chloropropane, chloropropane, DDT, kelthane, aldrin, endrin, dieldrin, endosulfan (benzoepin), heptachlor, heptachloroepoxide, malathion, methomyl, methoxychlor, mirex, nitrofen, toxaphen, trifluralin, alkylphenol (C5-C9), nonylphenol, octylnonylphenol, 4-octylphenol, bisphenol A, di-2-ethylhexyl phthalate, butylbenzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitrotoluene, octachlorostyrene, aldicarb, benomyl, kepone (chlordecone), manzeb (mancozeb), maneb, metiram, metoribuzin, cypermethrin, esfenvalerate, permethrin, vinclozolin, zineb, ziram, dipentylphthalate, dihexylphthalate and dipropylphthalate.

The biological substance is a substance selected from nucleic acid, protein, polysaccharide, lipid and composites thereof, more specifically, a substance containing a biological molecule selected from nucleic acid, protein, polysaccharide and lipid. The present invention can be applied to any substance as long as it contains a substance selected from DNA, RNA, aptamer, gene, chromosome, cell membrane, virus, antigen, antibody, lectin, hapten, hormone, receptors, enzyme, peptide, sphingoglycoside and sphingolipid. Further, bacteria and cells producing the above biological substance are the potential target substances.

In the potential target proteins, are included so-called disease markers. Examples of disease markers are: α-phetoprotein (AFP) which is an acidic glycoprotein produced by fetal hepatic cells and present in the fetal blood, and a marker of hepatocarcinoma (primary hepatic cancer), hepatoblastoma, metastatic liver cancer and yolk sac tumor; PIVKA-II, an abnormal prothrombin that appears on hepatic parenchymia disorder, and is confirmed to appear with hepatocarcinoma; BCA225, a glycoprotein being immunohistochemically a breast cancer specific antigen, which can be used as a marker of primary progressive breast cancer and recurrence/metastatic breast cancer; Basic fetoprotein (BFP), a basic fetal protein found in the human fetal serum, extracts of fetal intestine and brain tissue, a marker for ovary cancer, testicle tumor, prostatic tumor, pancreatic cancer, biliary tract cancer, hepatocarcinoma, renal carcinoma, pulmonary carcinoma, gastric carcinoma, bladder cancer and colon caner; CA15-3, an antigenic carbohydrate being used as a marker for advanced breast cancer, recurrent breast cancer, primary breast cancer and ovary cancer; CA19-9, an antigenic carbohydrate being used as a marker for pancreatic carcinoma, biliary tract cancer, gastric cancer, liver cancer, colon cancer and ovary cancer; CA125, an antigenic carbohydrate being used as a marker for ovary cancer (especially, serous cystandenocarcinoma), adenocarcinoma of the uterus corpus, fallopian tube cancer, cervix adenocarcinoma, pancreatic cancer, pulmonary carcinoma and colon cancer; CA130, an antigenic carbohydrate being used as a marker for epitherian ovarian cancer, fallopian tube cancer, pulmonary carcinoma, and pancreatic cancer; CA602, a core protein antigen being used as a marker for ovary cancer (especially, serous cystandenocarcinoma), adenocarcinoma of the uterus corpus and cervix adenocarcinoma; CA54/61 (CA546), a core polysaccharide-associated antigen, being used as a marker for ovary cancer (especially, serous cystandenocarcinoma), adenocarcinoma of the uterus corpus and cervix adenocarcinoma; carcinoembryonic antigen (CEA), a most widely used tumor-associated marker of colon cancer, gastric cancer, rectal cancer, biliary tract cancer, pancreatic cancer, breast cancer, uterus cancer and urinary system cancer, as a diagnostic aid; DUPAN-2, an antigenic carbohydrate being used as a marker of pancreatic cancer, biliary tract cancer, hepatocarcinoma, gastric cancer, ovary cancer and colon cancer; elastase 1, a pancreatic secretion proteinase that specifically hydrolyzes elastin, an elastic fiber of connection tissue constituting arterial wall or tendon, used a marker of pancreatic cancer, cancer in pancreatic cyst, and biliary tract cancer; immunosuppressive acidic protein (IAP), a glycoprotein present at a high concentration in the ascites and serum of human cancer patients, being used as a marker for pulmonary cancer, luekemya, esophargus cancer, pancreatic cancer, ovary cancer, renal cancer, biliary tract cancer, gastric cancer, bladder cancer, colon cancer, thyroid cancer and malignant lymphoma; NCC-ST-439, an antigenic carbohydrate being used as a marker for pancreatic cancer, biliary tract cancer, breast cancer, colon cancer, hepatocarcinoma, pulmonary adenocarcinoma and gastric cancer; γ-seminoprotein (γ-Sm), a glycoprotein being used as a marker for prostatic cancer; Prostate-specific antigen (PSA), a glycoprotein extracted from the human prostate tissue that exists only in the prostate tissue, hence a marker of prostatic cancer; prostatic acidic phosphatase (PAP), an enzyme which is secreted from the prostate to hydrolyze phosphate ester under acidic pH, and serves as a tumor marker for prostatic cancer; nerve specific enolase (NSE), a glycolysis enzyme present specifically in the nerve tissue and neuroendocrine cells, being used as a marker for pulmonary cancer, especially pulmonary small cell carcinoma, neuroblastoma, nervous system neoplasm, islet cell carcinoma, esophagus small cell cancer, gastric cancer, renal carcinoma and breast cancer; squamous cell cancer associated antigen (SCC antigen), a protein extracted and purified from of liver metastatis of cervix squamous cancer, being used as a marker for uterus cancer (cervix squamous cell cancer), pulmonary cancer, esophagus cancer, head and neck cancer and skin cancer; sialyl Le$^x$-i antigen (SLX), an antigenic carbohydrate being used as a marker for pulmonary adenocarcinoma, esophaguscancer, gastric cancer, colon cancer, rectal cancer, pancreatic cancer, ovary cancer and uterus cancer; SPan-1, an antigenic carbohydrate being used as a marker for pancreatic cancer, biliary tract cancer, liver cancer, gastric cancer and colon cancer; tissue polypeptide antigen (TPA), a single chain polypeptide being used as a marker for esophagus caner, gastric cancer, colorectal cancer, breast cancer, hepatocarcinoma, biliary tract cancer, pancreatic cancer, pulmonary cancer and uterus cancer, especially useful for diagnosis of advanced cancer in combination with other tumor markers, and for recurrence prediction and therapeutic process observation; sialyl Tn antigen, a core polysaccharide antigen being used as a marker for ovary cancer, metastatic ovary cancer, gastric cancer, colon cancer, biliary tract cancer, pancreatic cancer and pulmonary cancer; cytokeratin (CYFRA), a tumor marker used for detection of pulmonary non-small cell cancer, especially pulmonary squamous cell carcinoma; pepsinogen (PG), an inactive precursor of two pepsins (PB I and PG II), i.e., proteases secreted in the gastric juice, being used as a marker for gastric ulcer (especially low gastric ulcer), duodenal ulcer (especially, recurrent and refractory ulcer), brunneroma, Zolinger-Elison syndrome and acute gastritis; C-reactive protein (CRP), an acute phase reactive protein that varies with tissue lesion or infection in the serum, of which value becomes high if necrosis of the cardiac muscle occurs due to acute myocardial infarction etc.; serum amyloid A protein (SAA), an acute phase reactive protein that fluctuates in the serum according to the tissue lesion or infection; myoglobin, a heme protein of ca. 17500 molecular weight, mainly present in the heart muscle and the skeletal muscle, being used as a marker for acute myocardial infarction, muscular dystrophy, polymyositis and dermatomyositis; creatine kinase (CK: three isozymes of CK-MM derived from skeletal muscle, CK-BB derived from smooth muscle, and CK-MB derived from heart muscle, mitochondrial isozymes and immunoglobulin-binding CK (macro CK)), an enzyme that is released into the blood from the damaged cells, being used as a marker for acute myocardial infarction, hypothyroidism, progressive muscular dystrophy and polymyositis; troponin T, a protein of m.w.39000, forming a troponin complex with troponin I and troponin C on the thin filament of striated muscle participating control of muscle contraction, being used as a marker for rhabdomyolysis, myocarditis, cardiac infarction and kidney failure; and ventricle muscle myosin light chain I, a protein contained in any cell of skeletal muscle and cardiac muscle, as its increase in determining means disorder or necrosis of skeletal muscle and heart muscle, being used as a marker for acute myocardiac infarction, muscle dystrophy and kidney failure.

The target substance may be a bacteria species being an object of microbiological examination, such as *E. coli*, *Salmonella* and *Legionella* that are problematic for food and public health.

Further, viral proteins are included in the target substances such as hepatitis virus antigens of hepatitis viruses C and B, p24 antigen of HIV virus, pp56 antigen of cytomegaro virus (CMV) and E6 or E7 protein of HPV (human papilloma virus).

Detection of the target substance by using the measuring probe of the present invention is carried out by measuring the signal based on the binding between the detection component immobilized on the support and the target substance. The signal based on the binding between the detection component and the target substance is a signal that becomes detectable by the measuring probe means when the target substance is captured on the support surface by binding to the detection component held on the support surface. Thus the signal can be detected by using optical detection means, electric detection means or magnetic detection means, of which detection region is set onto the support surface. The target substance may be labeled directly with a chromophore, or a substance that specifically binds to the target substance may be labeled with a chromophore to indirectly attach the chromophore to the target substance. When the target substance is indirectly labeled with a chromophore, the substance that specifically binds to the target substance may be the same substance as the detecting component held on the support. For example, when an antibody against the target substance is held on the support, the same antibody labeled with a chromophore can be used as a secondary antibody only if the antibody is polyclonal antibody. Since in polyclonal antibody, antibodies recognizing different domains of the same antigen are included, the same antibody is used as the secondary antibody that binds to the target substance captured by the antibody held on the support as the detection component. As the chromophore that sends out signals for detection, fluorochromophore is preferably used. In a constitution where an optical waveguide is used as the support for the detection probe, the fluorochromophore is excited when the excitation light is introduced from the light source on the optical waveguide surface.

Preparation of Measuring Probe

The preparation process of the measuring probe according to the present invention is explained in the following. The process comprises a step of cross-linking protein molecules constituting the protein layer that is encircling the support. In other words, in this step, a protein layer containing protein molecules cross-linked to each other with a cross-linking agent is formed on the support to have a portion that encircles one axis of the support. For example, an antibody to the target substance is immobilized on the surface of a optical waveguide 2 of a measuring probe shown in FIGS. 2 and 3. Basically, immobilization is carried out by immersing the measuring probe in a solution of the antibody.

Although the protein can be immobilized by contacting the support with a solution containing both the protein and the cross-linking agent, it is more preferable to contact the support with a solution containing the cross-linking agent after the protein was physically adsorbed to the support.

The latter process may have a disadvantage of slow reaction rate due to the solid-liquid reaction, which, in contrast, may be advantageous in controlling the cross-linking reaction. The latter process is also useful when the cross-linking reaction in the liquid phase is difficult due to the pH or concentration of the material antibody solution. It also has an advantage that the unreacted reagent or by-products can be removed with ease.

In the former process, the concentration of the cross-linking agent is set to obtain a desired molar concentration ratio in the solution. In the latter process, the protein concentration on the support surface is first calculated, to which the cross-linking agent concentration is determined to be in the desired molar ratio. The protein concentration on the support surface can be calculated, for example, from the adsorbed protein mass, absorbance or the volume of the adsorption layer. The volume of the adsorption layer can be calculated from the coated area on the support and the layer thickness. The layer thickness can be determined by actual measurement using observatory means such as an electron microscope, or by estimation based on the theoretical size of the protein. It is preferable to experimentally confirm these values and the optimum molar ratio of the cross-linking agent in advance.

On the antibody immobilization, too high concentrations will cause antibody agglutination, and too low concentrations will limit the antibody amount immobilized on the probe surface. Usually, it is preferable to adjust the concentration in the range from 1 µg/ml to 100 µg/ml. Immersion is carried out at a low temperature such that denaturation of the antibody being a protein will not occur, that is, at 1-10° C., usually at around 4° C. Immersion is carried out for 15-30 hours, usually, for 24 hours.

The amount of the immobilized antibody on the probe can be estimated by calculating the difference of the antibody concentrations in the antibody buffer solution before and after the immersion. The antibody concentration in the antibody buffer solution can be determined an ordinary protein quantitating method such as the Lowry method and BCA method.

The surface antibody concentration is calculated from the concentration of the immobilized antibody. In this case, since the size of one molecule of ordinary antibody (Immunoglobulin G; IgG) is approximately 10 nm, the concentration is converted from the volume of the layer assuming that a layer of 10 nm thickness is coating the periphery of the probe.

A cross-linking agent is added to a proper ratio to the surface antibody concentration obtained by the above conversion. Addition is carried out by soaking the probe in a solution of the cross-linking agent in a buffer. In this case, prolonged immersion may cause denaturation of immobilized antibody, but too short immersion may cause insufficient addition of the cross-linking agent. Thus immersion for about 10 to 60 minutes at around 20 to 30° C. is preferable. The mol concentration of the cross-linking agent in the cross-linking reaction is preferably 1 to 5 times the mol concentration of the surface antibody. The protein layer may be formed to include at least one species selected from the group consisting of antibodies, antigen proteins, enzymes and receptors as the detection component for the target substance.

Various known cross-linking agents can be used, but those with less possibility of damaging the protein function are preferable. Preferable cross-linking agents are those having a reactive end which enables sufficient reaction in an ordinary temperature range. Such a reactive end includes aldehyde, carboxylic acid and carboxylic acid ester. Bifunctional cross-linking agents having these reactive ends can be suitably used. As a cross-linking agent having aldehyde at the both reactive ends, glutaraldehyde is suitably used. Carboxylic acid requires activation before use with a reagent such as carbodiimide. A preferred carboxylate ester is N-hydroxysuccinate imide ester. The span of the cross-linking agent (the chain length between the reactive ends) cannot be determined unambiguously, and it is necessary to choose the span according to the flexibility of the protein layer (related to adhesiveness), efficiency of the cross-linking reaction and water solubility.

It is also effective to stop the reaction using a suitable terminator in order to control the cross-linking reaction. For example, when the reaction cross-links the amino residues of the protein, an amine derivative is added as a terminator, such as tris(hydroxymethyl)aminomethane.

The present invention aims at enhancing the resistance of a protein layer against peeling, suitable for cases where the flow rate of a solution in contact with the probe, e.g., a sample solution, a reagent solution or acleaning solution, is relatively high.

The probe of the resent invention is specifically effective when applied to immunoassays using antibody molecules or fragments thereof as the protein. Usually, protein immobilization using a cross-linking agent such as glutaraldehyde is applied to enzymes such as glucose oxidase used in a blood sugar (glucose) sensor and tolylhydratase used in bioreactors. The reason why is that these enzymes subjected to immobilization are used in industry (industrial enzymes), excluding enzymes that may loose the activity on immobilization by glutaraldehyde cross-linking. On the other hand, antibodies are labile in comparison with industrial enzymes, although robust in comparison with ordinary in vivo enzymes. Thus the treatment of an antibody in the concentration range of the present invention is effective.

Conventionally, treatment with a cross-linking agent is roughly classified into treatment in saturated steam or treatment in a solution. In the former, it is clearly out of the concentration range of the present invention. In the latter, the treatment is carried out in an aqueous solution of usually containing 2 to 30% of cross-linking agent. Assumed that the mass of the protein immobilized on the support is similar to that of the present invention, the molar concentration of the cross-linking agent to the protein is 50- to 500-fold. Thus the object of the present invention is not achieved. That is, the present invention is remarkably effective for immobilization of a protein labile in comparison with industrial enzymes, especially an antibody or a fragment thereof.

Figure 2:
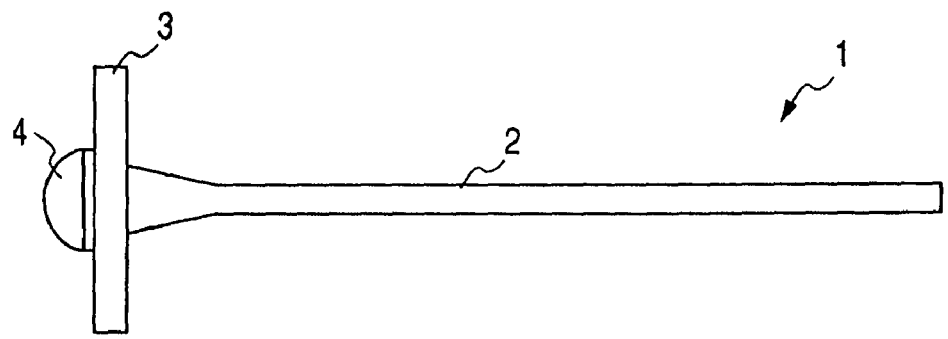
FIG. 2 is a schematic diagram showing a form of the measuring probe in Example.

FIG. 2 shows a configuration of a measuring probe being an embodiment of the present invention. The measuring probe 1 comprises a fiber-like portion 2, a flunge 3, and a convex portion 4.

Figure 3:
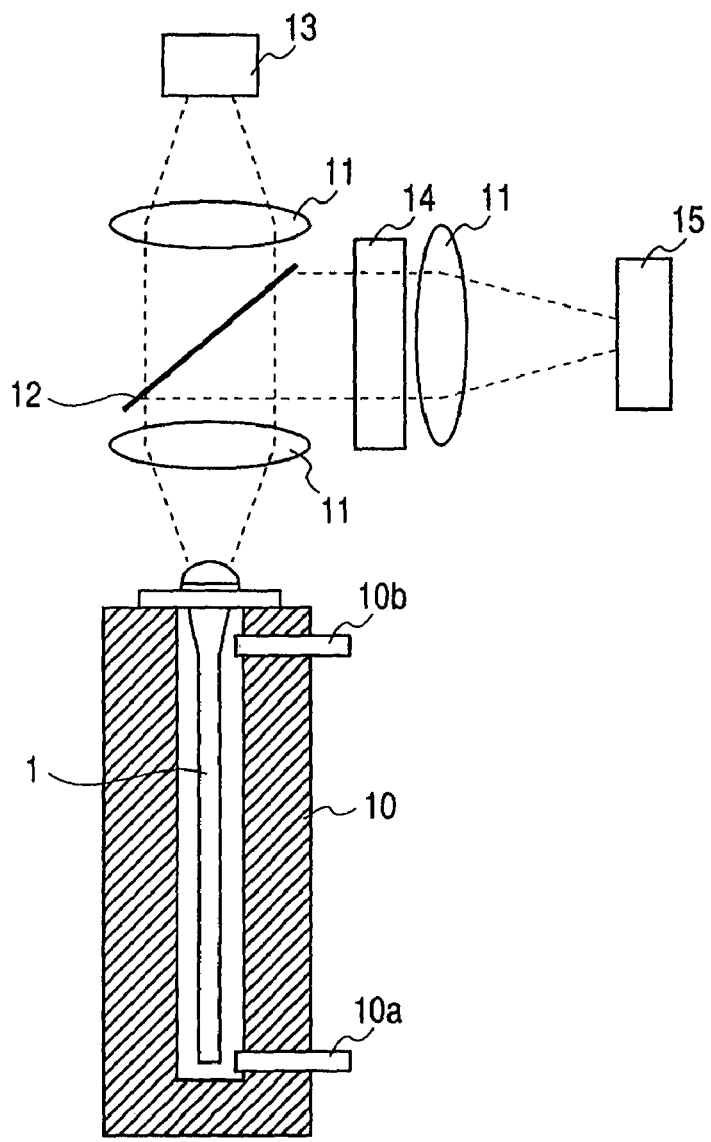
FIG. 3 is a schematic diagram showing a form of the measuring apparatus in Example.

FIG. 3 is a schematic diagram showing a specific configuration of a measuring apparatus using the above measuring probe. A flow cell 10 comprises an injection port 10a, and a discharge port 10b, constituted to be mounted in the apparatus in a state housing the fiber-like portion of the measuring probe 1 in the cell. The apparatus comprises a plurality of lenses 11, a half mirror 12, a semiconductor laser 13, an optical filter 14 and a photodiode 15 as a measuring optical system. The laser light emitted from the semiconductor laser 13 is concentrated by using lenses 11 and irradiated onto the convex portion of the measuring probe. The signal light from the convex portion is directed to the photodiode 15 by using the half mirror 12 for photometry of the signal intensity.

For other specific examples of measuring apparatus to use the probe of the present invention, U.S. Patent Application Publication 2006/0099111 A1 can be referred to.

Next, the present invention is explained in detail with the working example.

EXAMPLE

The present invention was applied to fluorescence immunoassay using a fiber-shaped probe. It should be noted that the following example is one of the best modes of the present invention, not to limit the application range of the present invention.

An anti-PASA (prostate grand-specific antigen) monoclonal antibody was diluted with a phosphate buffer (0.01 mol/L, pH 7.4) to 20 µl/ml, to which the fiber-like portion of the transparent polystyrene probe shown in FIG. 2 was immersed at 4° C. for 24 hours to physically adsorb and fix the antibody. The antibody was taken from a lot which had been known to frequently cause peeling from the support. This probe on which an antibody is fixed only by physical adsorption was used as a control probe (hereinafter referred to a non cross-linked probe).

The antibody concentration on the support surface fixed by physical adsorption was calculated from the reduction of the antibody concentration of the antibody solution after the adsorption treatment. The antibody concentration of a solution in which a plurality of probes were immersed was determined by using Protein Bioassay (BioRad) before and after the immersion, and the reduction amount was divided by the number of the immersed probes to determined the adsorbed amount of the antibody (0.052 µg/probe). The volume of the adsorption layer was calculated ($7.7 \times 10^{-10}$ L) from the area of the adsorption layer determined from the length of the immersed portion (35 mm) and the probe diameter (0.7 mm), the thickness determined based on the size of the antibody (assumed as a monoadsorption layer of 10 nm). From the above values, the average surface concentration of the antibody in the adsorption layer was estimated as $4.5 \times 10^{-4}$ mol/L.

Plural probes subjected for the adsorption fixation were immersed in a phosphate buffer containing 0.01 vol % of glutaraldehyde (1 mmol/l, about 2.2-fold molar concentration) for 30 minutes at 4° C., and then in an aqueous solution of tris(hydroxymethyl)aminomethane HCl (1 mol/L, pH 7.4) for 25 minutes at 25° C. These probes were air-dried to be used as the cross-linked probes.

Measurement using these probes was carried out using an apparatus shown in FIG. 3. The apparatus illustrated in FIG. 3 comprises an optical system to induce laser light from the semiconductor to the probe and at the same time to monitor the light emitted from the probe, and a liquid feeding system to supply the liquid to the probe surface.

Using 1 ng/ml PSA samples in a phosphate buffer, the following operation was carried out. Here, a phosphate buffer solution containing 0.1 wt % of polyoxyethylene (20) sorbitan monolaurate was used as a cleaning solution. The labeled antibody was prepared by reacting the capturing antibody with Cy5 BISFUNCTIONAL REACTIVE DYE (Ammersham Bioscience), and diluted with a phosphate buffer containing 1 wt % of bovine serum albumin to a 2 µg/ml solution.

(1) The sample is injected and then discharged after 5 minutes.

(2) The cleaning solution is injected and the signal light is measured in an immersed state (Signal A).

(3) The cleaning solution is discharged and a solution of the labeled antibody is injected which is then discharged after 5 minutes.

(4) The cleaning solution is injected and the signal light is measured in an immersed state (Signal B).

(5) Net measurement value is obtained by subtracting Signal A from Signal B.

The average measurement values were 29.8 picoampere, and 173 picoampere with non cross-linked probes and cross-linked probes respectively, which confirmed the increase in sensitivity.

The attenuation of signal intensity was monitored under the conditions where peeling may occur more frequently, that is, to the probes after signal detection, a phosphate buffer containing 0.5 wt % of polyoxyethylene (20) sorbitan monolaurate, instead of the cleaning solution, was fed at a rate of 10 ml/min for 5 minutes.

82% signal attenuation was observed with non cross-linked probes, but 50% signal attention with the cross-linked probes, which confirmed the prevention of peeling of the protein layer by cross-linking.

When the cross-linking agent was changed to bis(sulfosuccineimmidyl)suberate, similar results were obtained with a reaction time of 1 hour.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-160077, filed Jun. 8, 2006, which is hereby incorporated by reference herein in its entirety.

What is claimed is:

1. A measuring probe for detecting a specific analyte in a sample in contact with the sample, the probe comprising a support and a layer of a protein,
   wherein the support has a fiber-shaped portion, a flange portion, and a convex portion,
   wherein the protein layer has a circular cross-section so as to fully encircle the fiber-shaped portion,
   wherein the protein in the protein layer has been cross-linked by using a solution containing a cross-linking agent in a concentration 1 to 5 times as much as that of the protein, and
   wherein the protein layer is formed at the fiber-shaped portion.

2. The measuring probe according to claim 1, wherein the protein layer is formed to have a portion fully encircling an axis of elongation of the fiber-shaped portion.

3. The measuring probe according to claim 1, wherein the cross-linking agent is a bifunctional cross-linking agent, and the functional group for the cross-linking is selected from the group consisting of aldehyde, carboxylic acid and carboxylic acid ester.

4. The measuring probe according to claim 3, wherein the cross-linking agent is glutaraldehyde.

5. The measuring probe according to claim 1, wherein the protein contained in the protein layer is a component for detecting the analyte, the component being an enzyme or a receptor.

6. The measuring probe according to claim 1, wherein the protein contained in the protein layer is a component for detecting the analyte, the component being an antibody or an antigen or a fragment thereof.

7. The measuring probe according to claim 1, wherein a component for detecting the analyte is held on a subbing layer being the protein layer.

8. The measuring probe according to claim 7, wherein the detecting component is selected from the group consisting of antibody, antigen, enzyme, receptor, nucleobase, sugar chain and metal coordinate.

9. The measuring probe according to claim 1, wherein the support has a configuration selected from the group consisting of fiber-, brush- and mesh-like configurations.

10. The measuring probe according to claim 1, wherein the support is an optical waveguide.

11. The measuring probe according to claim 10, wherein the optical waveguide has, at an end thereof, an input/output section for optical signals.

12. The measuring probe according to claim 1, wherein the protein has been cross-linked by dipping only the fiber-shaped portion in the solution.

13. The measuring probe according to claim 1, wherein the convex portion is constructed to receive and emit light.

14. The measuring probe according to claim 1, wherein the molar ratio of the cross-linking agent to the protein is about 1:1 after the protein has been cross-linked.

15. The measuring probe according to claim 1, wherein the protein layer comprises a cross-linked polymer that provides space around the protein.

* * * * *